(12) United States Patent
Sekiguchi

(10) Patent No.: US 7,937,163 B2
(45) Date of Patent: May 3, 2011

(54) MEDICAL CONTROL DEVICE AND ITS SYSTEM

(75) Inventor: Kiyoshi Sekiguchi, Tokyo (JP)

(73) Assignee: Olympus Medical Systems Corp. (JP)

( * ) Notice: Subject to any disclaimer, the term of this patent is extended or adjusted under 35 U.S.C. 154(b) by 489 days.

(21) Appl. No.: 12/041,764

(22) Filed: Mar. 4, 2008

(65) Prior Publication Data
US 2009/0228813 A1    Sep. 10, 2009

(51) Int. Cl.
*G06F 19/00* (2006.01)
(52) U.S. Cl. .......................... 700/17; 600/300
(58) Field of Classification Search ............ 700/17, 700/83, 65; 600/151, 365, 300, 117, 133; 710/15, 771; 714/57; 348/65; 345/156, 345/858
See application file for complete search history.

(56) References Cited

U.S. PATENT DOCUMENTS

| | | | |
|---|---|---|---|
| 4,816,909 A | 3/1989 | Kimura et al. | |
| 5,871,439 A | 2/1999 | Takahashi et al. | |
| 6,120,435 A * | 9/2000 | Eino | 600/118 |
| 6,215,517 B1 | 4/2001 | Takahashi et al. | |
| 6,436,032 B1 * | 8/2002 | Eto et al. | 600/117 |
| 6,437,836 B1 * | 8/2002 | Huang et al. | 348/734 |
| 6,480,762 B1 * | 11/2002 | Uchikubo et al. | 700/253 |
| 6,491,628 B1 | 12/2002 | Kobayashi | |
| 6,597,374 B1 * | 7/2003 | Baker et al. | 715/717 |
| 6,690,409 B1 * | 2/2004 | Takahashi | 348/65 |
| 6,717,609 B2 * | 4/2004 | Sugimoto et al. | 348/74 |
| 7,001,330 B2 * | 2/2006 | Kobayashi | 600/118 |
| 2003/0093503 A1 * | 5/2003 | Yamaki et al. | 709/220 |

FOREIGN PATENT DOCUMENTS

| | | |
|---|---|---|
| DE | 37 42 900 | 7/1988 |
| DE | 198 16 481 | 10/1998 |
| DE | 101 26 587 | 12/2001 |
| EP | 0 534 198 | 3/1993 |
| JP | 8-123518 | 5/1996 |
| JP | 2003-190181 | 7/2003 |
| JP | 2006-43238 | 2/2006 |
| JP | 2007-185349 | 7/2007 |
| WO | WO 2006/039267 | 4/2006 |

OTHER PUBLICATIONS

Search Report issued by the European Patent Office in connection with corresponding application No. EP 09 001 245.1 on Jun. 24, 2009.

* cited by examiner

*Primary Examiner* — Kidest Bahta
(74) *Attorney, Agent, or Firm* — Ostrolenk Faber LLP

(57) ABSTRACT

A medical control system has a medical device, a medical control apparatus for controlling the medical device, and a display operation device for controlling the medical device. With the configuration, the medical device includes: a GUI setting information storage unit storing GUI setting information as setting information relating to design of a GUI screen configuring a graphical user interface (GUI) for controlling the medical device; a GUI setting information transmission unit transmitting the GUI setting information to the medical control apparatus. The medical control apparatus includes: a GUI generation unit generating a GUI screen image according to the transmitted GUI setting information; and an output unit outputting the generated GUI screen image to the display operation device.

14 Claims, 18 Drawing Sheets

404

GUI SCREEN PARAMETER INFORMATION FOR
DRAWING OPERATION BUTTON IMAGE DATA

| PARAMETER | VALUE |
|---|---|
| TYPE | CUT OUTPUT SET VALUE UP BUTTON |
| SHAPE | CIRCLE |
| POSITION X AXIS | 90 pixel |
| POSITION Y AXIS | 120 pixel |
| WIDTH | 20 pixel |
| HEIGHT | 20 pixel |
| LINE COLOR | BLACK |
| LINE THICKNESS | 3 pixel |
| PASTE COLOR | WHITE |

US 7,937,163 B2

MEDICAL CONTROL DEVICE AND ITS SYSTEM

FIELD OF THE INVENTION

The present invention relates to communication technology between a plurality of medical devices and a medical control apparatus for controlling these medical devices.

BACKGROUND OF THE INVENTION

Recently, an endoscope operation and an endoscope diagnosis are performed using an endoscope operation system provided with a plurality of medical devices. An endoscope operation system includes a plurality of medical devices such as an endoscope device, a light source device, an electrical surgical device, a touch panel, a monitor, etc. and a system controller for centrally controlling the medical devices. The system controller can display a setting screen for control item of a medical device to be controlled and an operation mode on a touch panel or a display device of a monitor. The setting screen displayed on the display device is loaded with a graphical user interface (hereinafter referred to simply as a GUI) operated with a pointer etc, and is designed for easy operation for a user.

The Japanese Published Patent Application No. 2003-190181 discloses a controller capable of receiving icon data (image data) and data for an operation screen from a medical device and displaying a GUI operation screen.

In the Japanese Published Patent Application No. 2003-190181, image data is stored in the memory of a medical device, and transmitted to the controller when the electric supply is turned on. Since an operation screen is generated from image data, flexible design can be prepared, and a comprehensible operation screen can be generated to shorten the operating time.

SUMMARY OF THE INVENTION

The medical control system according to the present invention includes a medical device, a medical control apparatus for controlling the medical device, and a display operation device for controlling the medical device.

With the configuration, the medical device includes:

a GUI setting information storage unit for storing GUI setting information as setting information relating to the design of a GUI screen configuring a graphical user interface (GUI) for controlling the medical device;

a GUI setting information transmission unit for transmitting the GUI setting information to the medical control apparatus, and the medical control apparatus includes:

a GUI generation unit for generating a GUI screen image according to the transmitted GUI setting information; and an output unit for outputting the generated GUI screen image to the display operation device.

The medical control apparatus according to the present invention includes:

a reception unit for receiving GUI setting information transmitted from a medical device as setting information relating to a design of a GUI screen configuring a graphical user interface (GUI) for controlling the medical device;

a GUI generation unit for generating a GUI screen image according to the GUI setting information;

an output unit for outputting the generated GUI screen image to the display operation device.

The medical control system according to the present invention includes:

a medical device; a medical control apparatus for controlling the medical device; and a display operation device for controlling the medical device. With the configuration, the medical device includes:

a GUI image data storage unit for storing graphical user interface (GUI) image data to be displayed on the display operation device, and identification information for identification of the GUI image data; and a transmission unit for transmitting the identification information. With the configuration, the medical control apparatus includes:

a GUI image data identification storage unit for storing the identification information and GUI image data corresponding to the identification information;

a determination unit for determining whether or not identification information matching the identification information transmitted from the medical device is stored in the GUI image data identification storage unit;

a GUI generation unit for generating a GUI image based on the GUI image data corresponding to the identification information when it is determined that the identification information matching the received identification information is stored in the GUI image data identification storage unit; and an output unit for outputting the generated GUI image to the display operation device.

The medical control apparatus according to the present invention includes:

a GUI image data identification storage unit for storing graphical user interface (GUI) image data and identification information for identification of the GUI image data;

a determination unit for receiving identification information transmitted from a medical device, and determining whether or not identification information matching the identification information is stored in the GUI image data identification storage unit;

a GUI generation unit for generating a GUI image based on the GUI image data corresponding to the identification information when it is determined that identification information matching the received identification information is stored in the GUI image data identification storage unit; and output unit for outputting the generated GUI image to the display operation device.

The medical control system according to the present invention includes a medical device, a medical control apparatus for controlling the medical device, and a display operation device for controlling the medical device. With the configuration, the medical device includes:

a storage unit for storing first GUI screen data relating to a predetermined function among GUI image data configuring a graphical user interface (GUI) for controlling the medical device, and second GUI screen data as GUI screen data other than the first GUI screen data;

a transmission unit for sequentially transmitting the first GUI screen data and the second GUI screen data, and the medical control apparatus includes:

a reception unit for sequentially receiving the first GUI screen data and the second GUI screen data;

a GUI generation unit for generating GUI screen image based on the received GUI screen data; and an output unit for outputting the GUI screen image to the display operation unit, and after completely receiving the first GUI screen data, the GUI generation unit generates the first GUI screen image based on the first GUI screen data, displays the image on the display operation unit, and after completely receiving the second GUI screen data, the second GUI screen image is generated based on the first GUI screen data and the second GUI screen data, and displayed on the display operation unit.

DETAILED DESCRIPTION OF THE INVENTION

Figure 1:
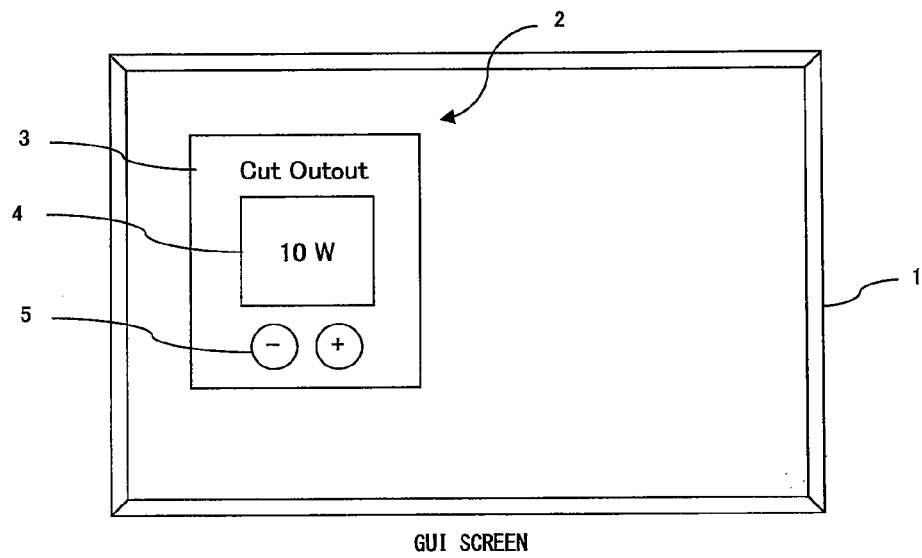
FIG. 1 shows image data configuring the conventional operation screen.
Figure 1:
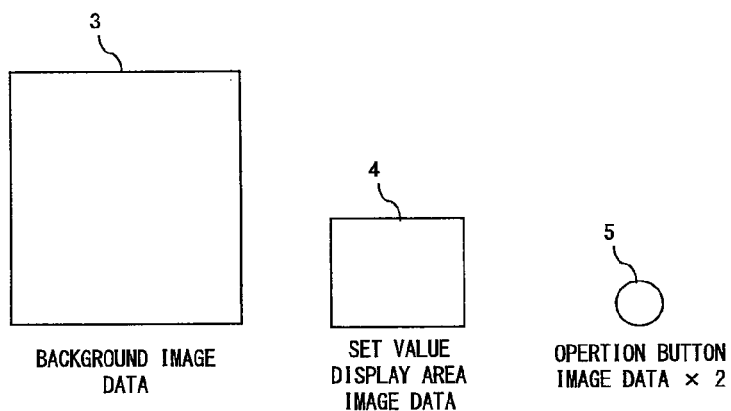

FIG. 1 shows image data configuring the conventional operation screen. Conventionally, when an operation screen image 2 is displayed in the display area of an operation panel 1, four kinds of image data (bit map file), that is, background image data 3, set value display area image data 4, and two pieces of operation button image data 5, are required.

However, since these pieces of image data are large in volume, it takes a long communication time when a medical device transmits data to a controller. In addition, when a plurality of medical devices are simultaneously powered up, it takes long time for communication and processing because the controller has to receive and process plural pieces of data transmitted from the medical devices. Therefore, during the time, the controller cannot control the medical devices, thereby interfering with the smooth progress of the operation. In an endoscopic surgery, since it is common that the power supplies of medical devices are collectively turned on by a central power supply, the above phenomenon can easily occur.

Then, according to the embodiments of the present invention, when a screen to control a medical device is displayed on the display operation screen, image data corresponding to the screen is transmitted. At this time, the communication load between the controller and the medical device is reduced in the following medical control system.

Figure 2:
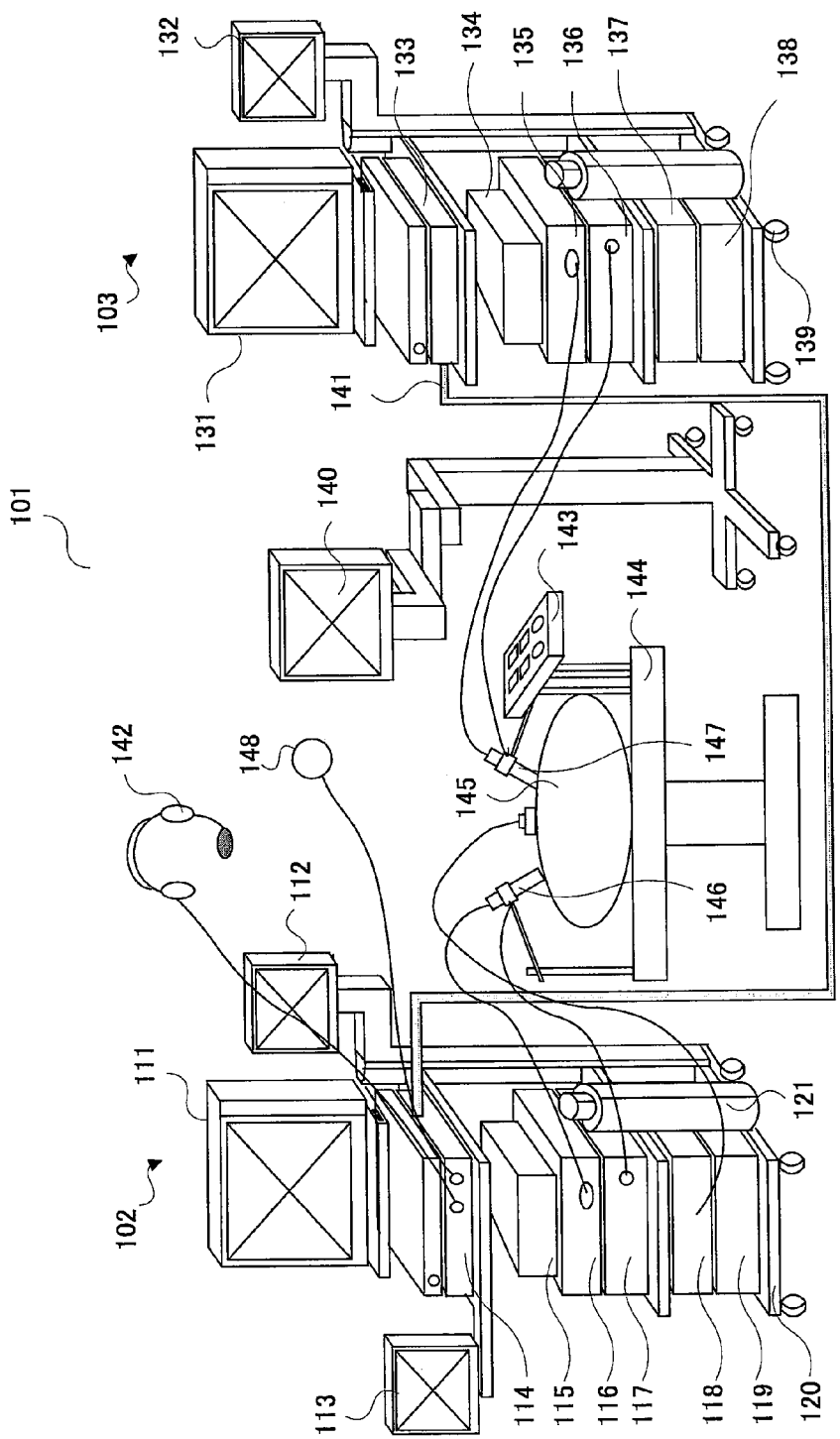
FIG. 2 shows the entire configuration of the endoscope operation system according to the first through third embodiments.

FIG. 2, shows the entire configuration of the endoscopic operation system according to an embodiment of the present invention. An endoscopic operation system 101 is provided on both sides of a bed 144 of a patient 145 a first endoscope operation system 102, a second endoscopic operation system 103, and an operator's wireless remote controller 143.

In the endoscopic operation systems 102 and 103, a plurality of endoscope medical devices for performing an observation, inspection, process, record, etc. are loaded into a first trolley 120 and a second trolley 139. A movable stand is loaded with an endoscope display panel 140.

The first trolley 120 includes an endoscope display panel 111, a central display panel 112, a central operation panel device 113, a system controller 114, a recorder 115, a video processor 116, an endoscope light source device 117, an insufflation device 118, and an electrical surgical device 119.

The central operation panel device 113 is arranged in an unsterilized area, and nurses etc. centrally perform operations of medical devices. A mouse, a touch panel, etc. not shown in the attached drawings can be provided for the device. Using the central operation panel device 113, a medical device can be centrally managed, controlled, and operated.

Each medical device is connected to the system controller 114 through a communication cable such as a serial interface cable etc. not shown in the attached drawings to perform bi-directional communications with a system controller.

Additionally, a head set type mike 142 can be connected to the system controller 114. The system controller 114 recognizes the voice input from the head set type mike 142, and can control each device by the voice of an operator. Furthermore, a speaker 148 can be connected to the system controller 114.

The endoscope light source device 117 is connected to a first endoscope 146 through a light guide cable for transmitting illumination light. When the illumination light of the endoscope light source device 117 is supplied to the light guide of the first endoscope 146, it illuminates the affected part etc. in the belly of the patient 145 into which the insertion part of the first endoscope 146 is needled.

The optical image data captured by the camera head of the first endoscope 146 is transmitted to the video processor 116 through the camera cable. The optical image data is signal-processed in the signal processing circuit in the video processor 116, thereby generating a video signal.

The insufflation unit 118 provides $CO_2$ gas from a gas cylinder 121 into the belly of the patient 145.

The second trolley 139 is loaded with an endoscope display panel 131, a central display panel 132, a expansion unit 133, a recorder 134, a video processor 135, an endoscope light source device 136, and the other medical devices 137 and 138 (for example, an ultrasonic processing device, a lithotripsy device, a pump, a shaver, etc.). Each device is connected to the expansion unit 133 via a cable not shown in the attached drawings for enabling bi-directional communications. The system controller 114 is connected to the expansion unit 133 by a expansion cable 141.

The endoscope light source device 136 is connected to a second endoscope 147 through a light guide cable for transmitting illumination light. The illumination light of the endoscope light source device 136 is supplied to the light guide of the second endoscope 147. Then, it illuminates the affected part etc. in the belly of the patient 145 into which the insertion part of the second endoscope 147 is needled.

The optical image data captured by the camera head of the second endoscope 147 is transmitted to the video processor 135 through a camera cable. The optical image data is signal-processed by the signal processing circuit in the video processor 135, thereby generating a video signal. Then the video signal is output to the endoscope display panel 131, and an endoscope image of an affected part etc. is displayed on the endoscope display panel 131.

The system controller 114 can also be controlled by the operator's wireless remote controller 143 with which an operator performs the operation of the device from a sterilized area. In addition, the first trolley 120 and the second trolley 139 can be loaded with other devices (for example, a printer, an ultrasonic observation device, etc.).

Figure 3:
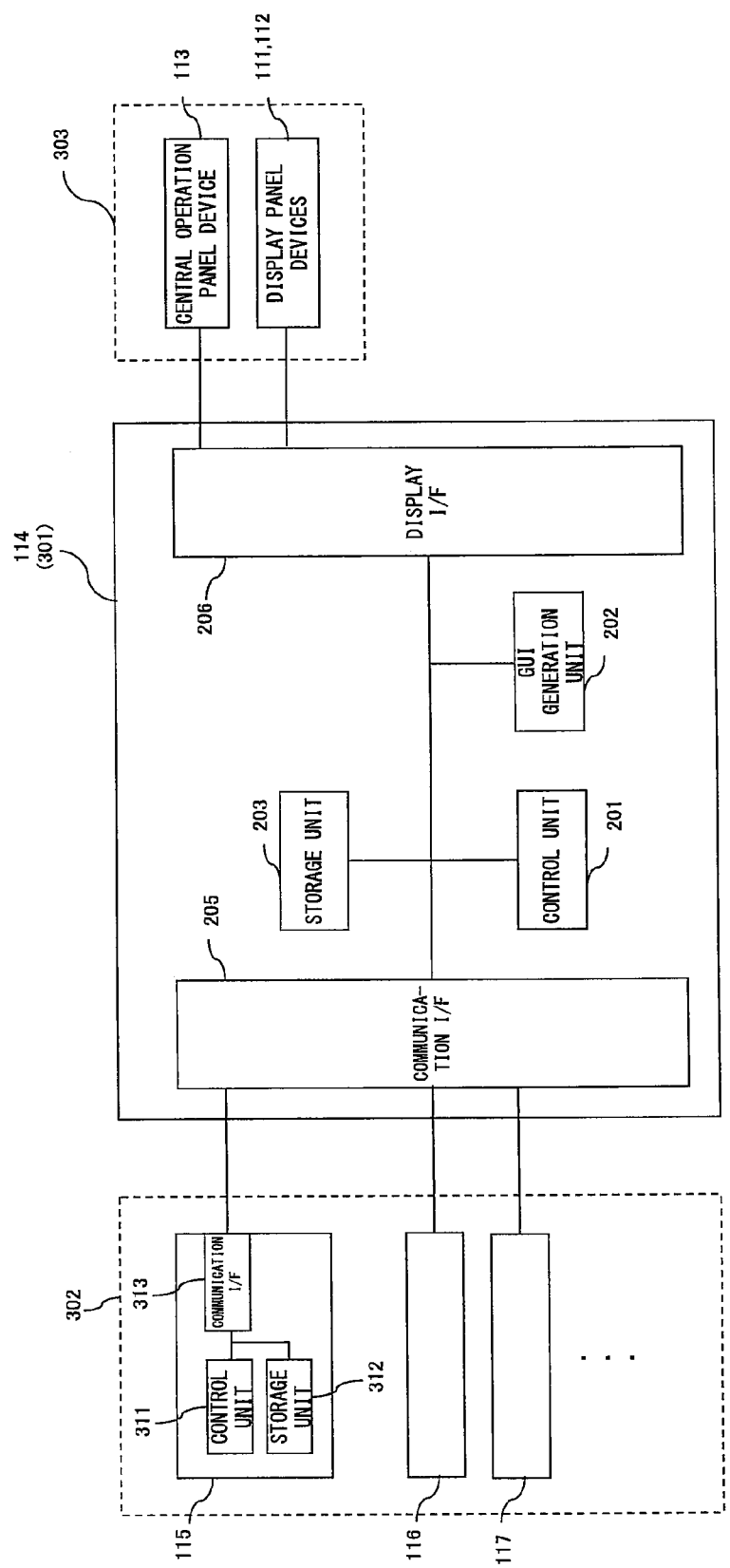
FIG. 3 shows the outline of the internal configuration of a system controller 114 according to the first through third embodiments.

FIG. 3 shows the outline of the internal configurations of the system controller 114 and a medical device according to the present embodiment. The display panel devices 111 and 112, the central operation panel device 113, and the medical devices 302 (the recorder 115, the video processor 116, the endoscope light source device 117, the insufflation device 118, the electrical surgical device 119, etc.) are connected to the system controller 114 (hereinafter referred to as a controller 301).

The controller 301 includes a control unit 201, a GUI generation unit 202, a storage unit 203, a communication I/F 205, a display I/F 206, and a bus 207 for connecting these components.

The communication I/F 205 is an interface for communication with the medical device 302 such as the recorder 115, the video processor 116, the endoscope light source device 117, the insufflation device 118, the electrical surgical device 119, etc.

The storage unit 203 is memory such as RAM (random access memory), ROM (read only memory), etc. for use in various processes, or a hard disk drive (HDD) for storing a large volume of data.

The control unit 201 includes CPU, etc. for executing various processing programs stored in the storage unit 203. The control unit 201 controls various devices etc. configuring the controller 301, and controls the communications with the medical devices 302.

The GUI generation unit 202 performs various image processing based on the control by the control unit 201, and structures an operation screen for displaying on a display unit 303 such as the central operation panel device 113, the display panel devices 111 and 112, etc.

The display I/F 206 outputs the GUI image data generated by the GUI generation unit 202 to the central operation panel device 113 and the display panel devices 111 and 112, and receives an operation signal from the central operation panel device 113 and the display panel devices 111 and 112.

The medical device 302 is provided with a control unit 311, a storage unit 312, and a communication I/F 313. The storage unit 312 is memory such as RAM (random access memory), ROM (read only memory), etc. for use in various processes, or a hard disk drive (HDD) for storing a large volume of data.

The storage unit 312 stores data relating to the GUI to be displayed by the controller 301 on the display unit 303.

The control unit 201 includes a CPU etc. for executing various processing programs stored in the storage unit 312. The control unit 201 controls various devices etc. configuring the medical device 302, and controls the communications with the controller 301. The communication I/F 313 is an interface for communication with the controller 301.

First Embodiment

In the system environment described above, the medical device 302 stores in advance the minimal parameters required to draw image data to be displayed on the display unit 303 are stored in the format of a small-capacity text file etc. as GUI screen parameter information according to the present embodiment. The controller 301 receives the GUI screen parameter information from the medical device 302, draws image data to be displayed on the display unit 303 according to the GUI screen parameter information, and displays the data on the display unit 303. The present embodiment is described below in detail.

Figure 4A:
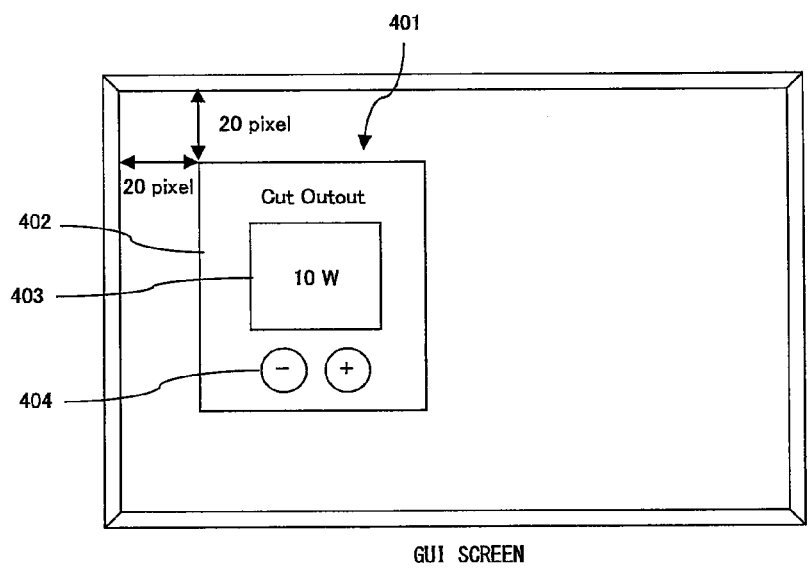
FIG. 4A shows an example of an operation screen image data 401 according to the first embodiment.
Figure 4B:
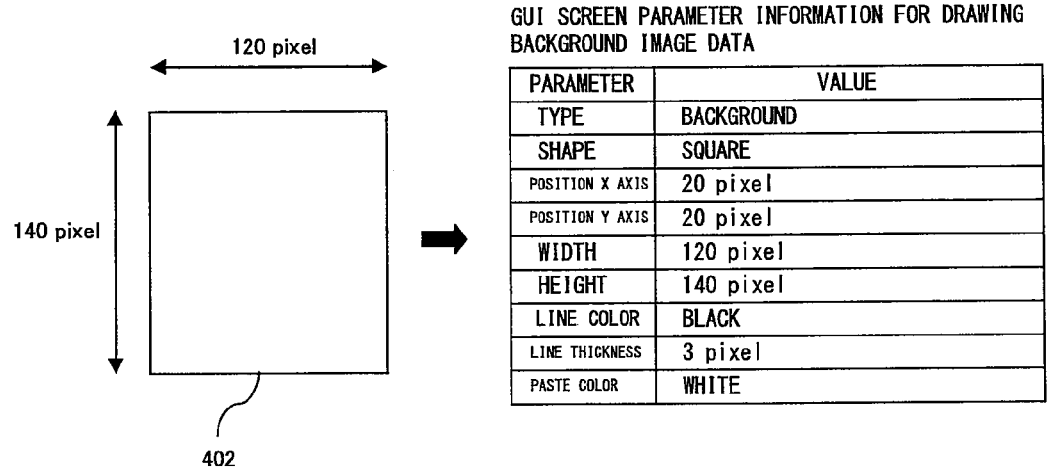
FIG. 4B shows a parameter for drawing a background image data 402 according to the first embodiment.
Figure 4C:
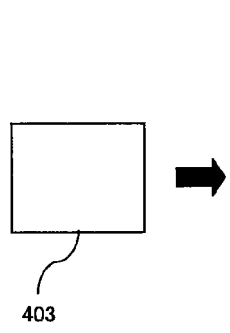
FIG. 4C shows a parameter for drawing a set value display area image data 403 according to the first embodiment.
Figure 4D:
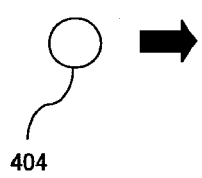
FIG. 4D shows a parameter for drawing an operation button image data 404 according to the first embodiment.

FIG. 4A shows an example of operation screen image data 401 according to the present embodiment. FIGS. 4B through 4D show examples of parameters for drawing image data of the parts configuring the operation screen shown in FIG. 4A.

FIG. 4B shows the parameters for drawing background image data 402. FIG. 4C shows the parameters for drawing set value display area image data 403. FIG. 4D shows the parameters for drawing operation button image data 404. These image data can be represented by the parameters about "type", "shape", "position X axis", "position Y axis", "width", "height", "line color", "line thickness", and "paste color". These parameters are stored in advance as GUI screen parameter information in the format of a small-capacity text file etc. in the storage unit 312 of the medical device 302.

Figure 5:
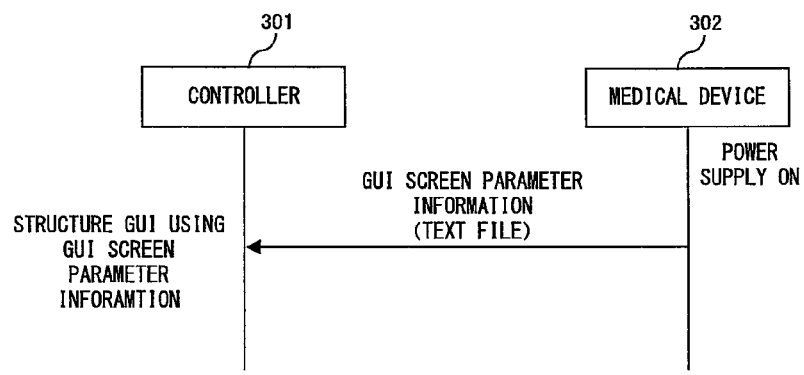
FIG. 5 is an explanatory view of transmitting GUI screen parameter information from a medical device to a controller 301 according to the first embodiment.

FIG. 5 is an explanatory view of transmitting the GUI screen parameter information from a medical device to the controller 301 according to the present embodiment. When the medical device 302 is turned ON, the control unit 311 immediately reads the GUI screen parameter information (text file) from the storage unit 312, and transmits the information to the controller 301 through the communication I/F 313. The controller 301 receives the GUI screen parameter information through the communication I/F 205. The control unit 201 transmits the GUI screen parameter information to the GUI generation unit 202. The GUI generation unit 202 generates GUI screen image according to the GUI screen parameter information. The generated GUI screen image is output to the display unit 303 through the display I/F 206 and displayed on the display unit 303.

Figure 6A:
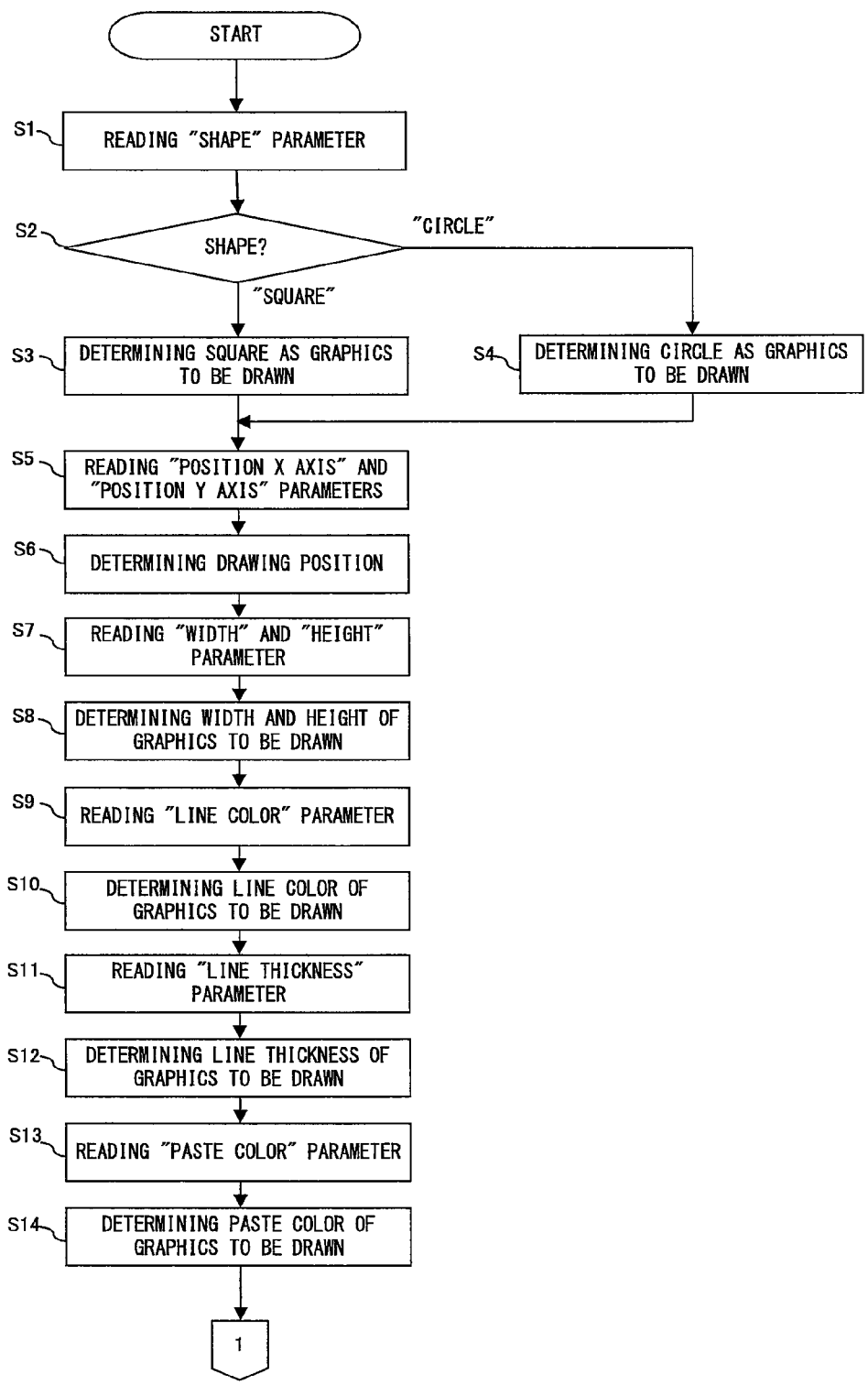
FIG. 6A is a flowchart (1) of structuring a GUI from GUI screen parameter information according to the first embodiment.
Figure 6B:
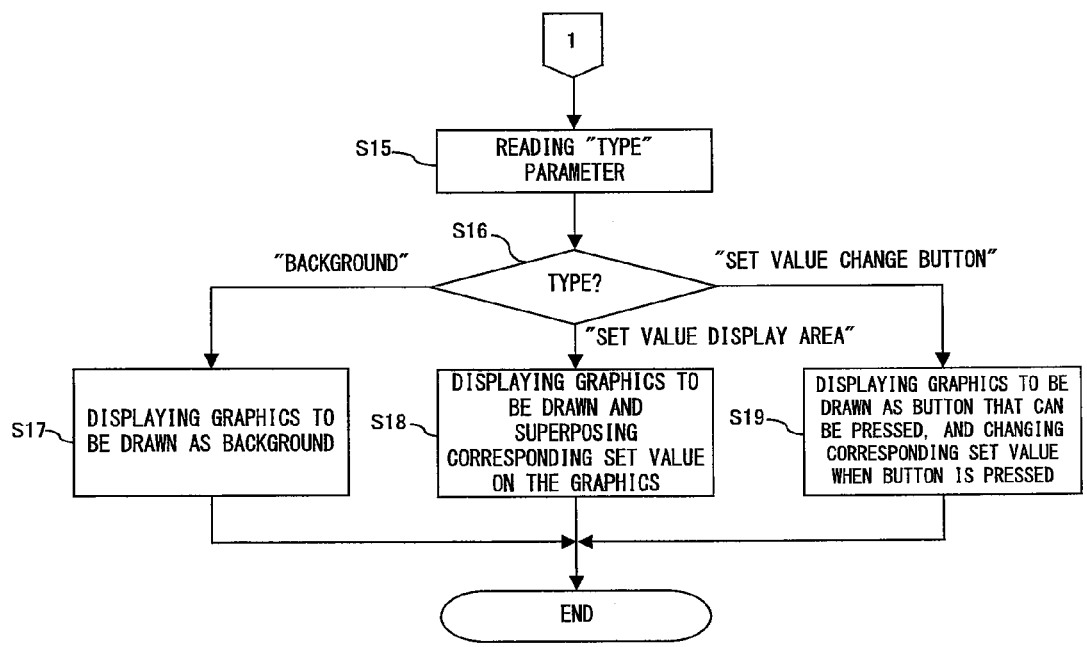
FIG. 6B is a flowchart (2) of structuring a GUI from GUI screen parameter information according to the first embodiment.

FIGS. 6A and 6B are flowcharts of configuring a GUI based on the GUI screen parameter information according to the present embodiment. As described above, when the control unit 201 receives GUI screen parameter information from the medical device 302, it allows the GUI generation unit 202 to execute the flow. The GUI generation unit 202 sequentially reads the parameters from the GUI screen parameter information and analyzes them, generates image data corresponding to the GUI screen parameter information, combines the image data, and structures GUI screen image.

First, the GUI generation unit 202 reads a "type" parameter from the GUI screen parameter information (S1), and determines the shape of the graphics to be drawn (S2). If the "shape" parameter refers to a "square", the GUI generation unit 202 determines the graphics to be drawn as a square (S3). It determines the graphics as a circle if the parameter refers to a "circle" (S4).

Next, the GUI generation unit 202 reads the "position X axis" parameter and the "position Y axis" parameter (S5), and determines the position of the graphics to be drawn on the display screen of the display unit 303 (S6). Next, the GUI generation unit 202 reads the "width" parameter and the "height" parameter (S7), and determines the width and the height of the graphics to be drawn (S8). Then, the GUI generation unit 202 reads the "line color" parameter (S9), and determines the color of the line of the graphics to be drawn (S10). Next, the GUI generation unit 202 reads the "line thickness" parameter (S11), and determines the thickness of the line of the graphics to be drawn (S12). Then, the GUI generation unit 202 reads the "paste color" parameter (S13), and determines the paste color of the graphics to be drawn (S14).

Next, the GUI generation unit 202 reads the "type" parameter (S15), and determines the type of the graphics to be drawn (S16). If the "type" parameter refers to a "background", the GUI generation unit 202 allows the graphics to be drawn to be displayed as the background (S17). If the "type" parameter refers to a "set value display area", the GUI generation unit 202 displays graphics to be drawn, and superposes a corresponding set value on the graphics (S18). If the "type" parameter refers to a "set value change button", the GUI generation unit 202 displays the graphics to be drawn as a button that can be pressed, and changes a corresponding set value when the button is pressed.

Thus, the medical control system includes the medical device 302, a medical control apparatus (controller 301) for controlling the medical device, and a display operation device (display unit 303) for controlling the medical device.

The medical device includes a GUI setting information storage unit (storage unit 312), and a GUI setting information transmission unit (communication I/F 313). The GUI setting information storage unit stores GUI setting information (GUI screen parameter information) as setting information relating to the design of the GUI screen configuring the graphical user interface (GUI) for control of the medical device. The GUI setting information transmission unit transmits the GUI setting information to the medical control apparatus.

The medical control apparatus includes a GUI generation unit (GUI generation unit 202), and an output unit (display I/F 206). The GUI generation unit generates a GUI image according to the transmitted GUI setting information. The output unit outputs the generated GUI image to the display operation device.

The GUI setting information is text data (GUI screen parameter information) for forming parts configuring the GUI screen and the information is generated for each part. The GUI generation unit analyzes each piece of received GUI setting information, generates an image of the parts corresponding to each piece of GUI setting information, combines the parts images, and forms the GUI image.

With the above-mentioned configuration, the volume of data to be transmitted from the medical device 302 to the controller 301 can be reduced.

With the present embodiment, a medical device transmits GUI screen parameter information defined in the text data format of [shape], [position], [width], [height], [line color], [line thickness], [paste color], etc. of each portion of the GUI to be displayed. A controller can structure a GUI screen according to the received GUI screen parameter information. Thus, it is not necessary to store image data in the medical device. In addition, the volume of data can be reduced without affecting the comprehensibility of the operation screen. Furthermore, by reducing the volume of data to be transmitted, the communication time can be shortened. Therefore, an operation can be smoothly performed. Furthermore, a large-capacity memory is not required for a medical device, thereby reducing the entire cost.

In the present embodiment, graphics are drawn according to the GUI screen parameter information, but the present invention is not limited to this application. For example, a controller holds in advance template information about a plurality of graphics, and the size, position, etc. of the graphics are adjusted according to the GUI screen parameter information.

Second Embodiment

In the present embodiment, the medical control apparatus requests to transmit GUI screen data to a medical device according to identification information transmitted from the medical device after the GUI screen data received from the medical device is associated with identification information and stored as described below. Since the system environment of this embodiment is the same as shown in FIGS. 2 and 3, its explanation is omitted here.

Figure 7:
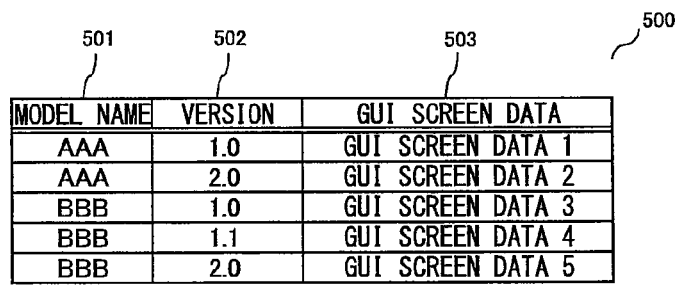
FIG. 7 shows an example of a GUI screen data identification table 500 according to the second embodiment.

FIG. 7 shows an example of a GUI screen data identification table 500 according to an embodiment of the present invention. The GUI screen data identification table 500 is stored in the storage unit 203 of the controller 301. The GUI screen data identification table 500 is configured by data items of, for example, a "model name" 501, a "version name" 502, a "GUI screen data" 503. The "model name" 501 stores the model name of a medical device. The "GUI screen data" 503 stores the GUI screen data of the medical device corresponding to the "model name" 501. The "version" 502 stores the version information about the GUI screen data stored in the "GUI screen data" 503.

The controller 301 associates the GUI screen data received from the medical device 302 with identification information (information as a combination of a model name and a version name), and stores the data in the GUI screen data identification table 500.

Figure 8A:
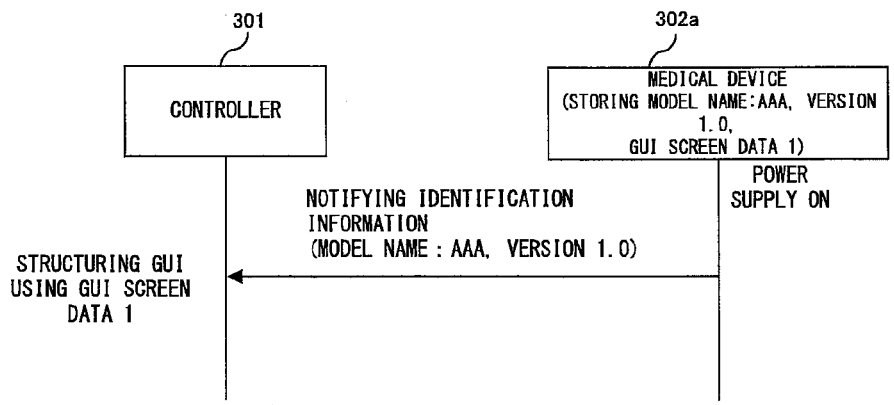
FIG. 8A is an explanatory view of transmitting GUI screen parameter information to a controller 301 from a medical device according to the second embodiment.
Figure 8B:
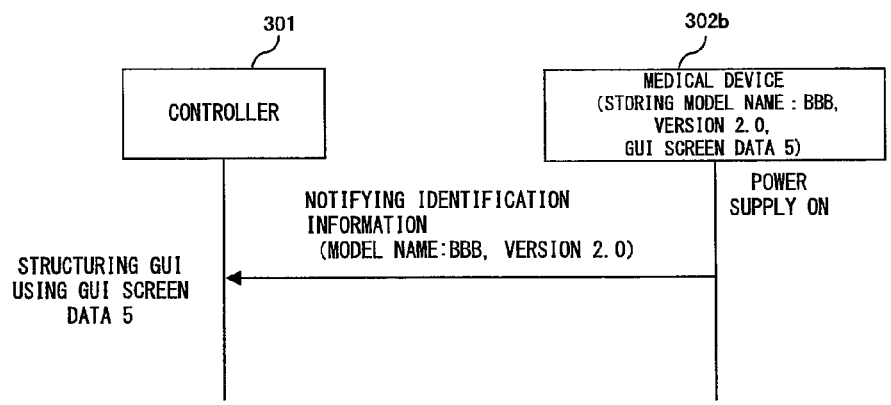
FIG. 8B is an explanatory view of transmitting GUI screen parameter information to a controller 301 from a medical device according to the second embodiment.
Figure 8C:
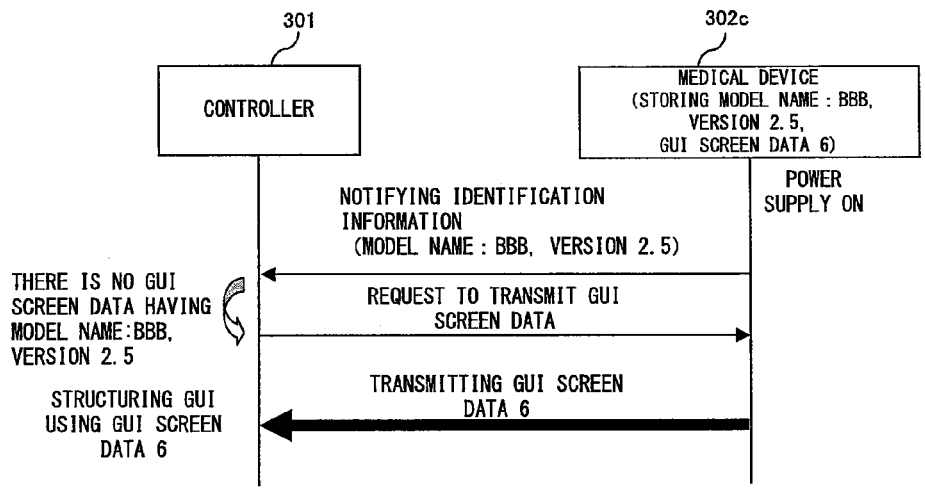
FIG. 8C is an explanatory view of transmitting GUI screen parameter information to a controller 301 from a medical device according to the second embodiment.

FIGS. 8A through 8C are explanatory views showing the transmission of GUI screen parameter information from the medical device 302 to the controller 301 according to the present embodiment. Medical devices 302a, 302b, and 302c store the "model name" as identification information, the "version" of the GUI screen data, and the GUI screen data corresponding to the identification information in the storage unit 312.

In FIG. 8A, the medical device 302a stores "model name: AAA, version 1.0, GUI screen data 1". When the medical device 302a is turned on, the control unit 311 reads the identification information D1 (model name: AAA, version 1.0) from the storage unit 312, and notifies the controller 301 of the information through the communication I/F 313.

The controller 301 receives identification information D1 through the communication I/F 205. The control unit 201 searches GUI screen data having matching "model name" and "version" with the received identification information D1 from the GUI screen data identification table 500 in the storage unit 203. Since the GUI screen data identification table 500 shown in FIG. 7 includes the "model name: AAA, version 1.0" matching the identification information D1, the control unit 201 reads the GUI screen data 1 corresponding to the "model name: AAA, version 1.0", and transmits the data to the GUI generation unit 202. The GUI generation unit 202 generates GUI screen image based on the GUI screen data 1.

The generated GUI screen image is output to the display unit 303 through the display I/F 206, and is displayed on the display unit 303.

In FIG. 8B, the medical device 302b stores "model name: BBB, version 2.0, GUI screen data 5". When the 302b is turned on, the control unit 311 reads the identification information D2 (model name: BBB, version 2.0) from the storage unit 312, and notifies the controller 301 of the information through the communication I/F 313. The controller 301 receives the identification information D2 through the communication I/F 205. The control unit 201 searches the GUI screen data of the "model name" and "version" matching the notified identification information from the GUI screen data identification table 500 in the storage unit 203. Since the GUI screen data identification table 500 shown in FIG. 7 includes the "model name: BBB, version 2.0" matching the identification information D1, the control unit 201 reads the GUI screen data 5 corresponding to the "model name: BBB, version 2.0", and transmits the data to the GUI generation unit 202. The GUI generation unit 202 generates the GUI screen image based on the GUI screen data 5. The generated GUI screen image is output to the display unit 303 through the display I/F 206, and displayed on the display unit 303.

In FIG. 8C, the medical device 302c stores "model name: BBB, version 2.5, GUI screen data 6". When the medical device 302c is turned on, the control unit 311 reads the identification information D3 (model name: BBB, version 2.5) from the storage unit 312, and notifies the controller 301 of the information through the communication I/F 313. The controller 301 receives the identification information D3 through the communication I/F 205. The control unit 201 searches the GUI screen data of the "model name" and the "version" matching the notified identification information D3 from the GUI screen data identification table 500 in the storage unit 203. The GUI screen data identification table 500 shown in FIG. 7 does not include the GUI screen data of the "model name: BBB, version 2.5". In this case, the controller 301 requests the medical device 302c to transmit the GUI screen data corresponding to the identification information D3.

Upon receipt of the transmission request, the medical device 302c transmits GUI screen data 6 corresponding to the identification information D3 to the controller 301. The control unit 201 receives the GUI screen data 6, associates the GUI screen data 6 with the identification information D3, and stores the data in the GUI screen data identification table 500. Then, the control unit 201 transmits the GUI screen data 6 to the GUI generation unit 202. The GUI generation unit 202 generates GUI screen image based on the GUI screen data 6. The generated GUI screen image is output to the display unit 303 through the display I/F 206 and displayed on the display unit 303.

Thus, when the controller 301 holds the GUI screen data corresponding to the identification information matching the received identification information (model name and version name), the GUI screen data is not transmitted from the medical device 302 to the controller 301. Therefore, a communication load can be suppressed.

Figure 9:
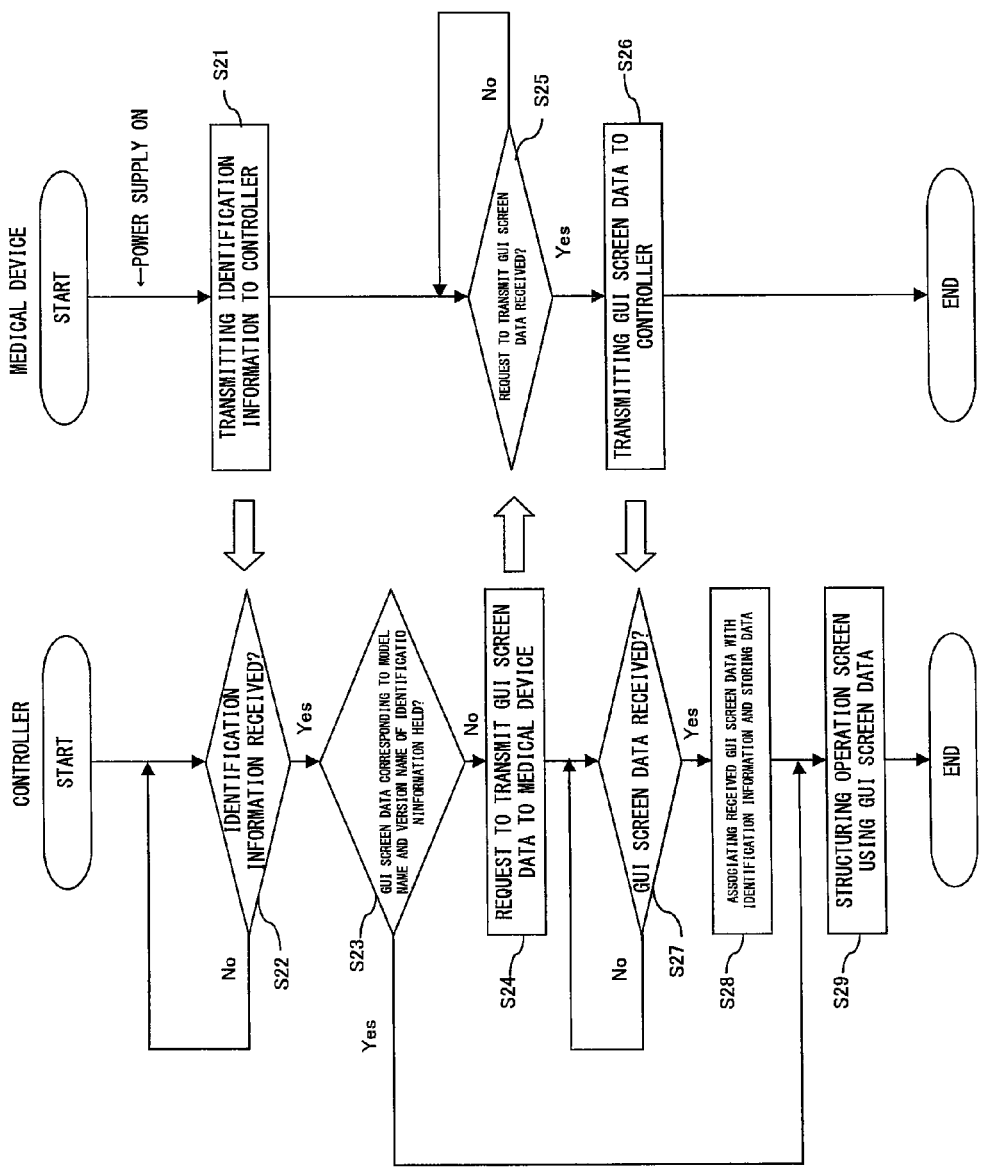
FIG. 9 is an operation flowchart of the controller and the medical device according to the second embodiment.

FIG. 9 is a flowchart of the operation of the controller 301 and the medical device 302 according to the present embodiment. The medical device 302 stores "model name: XXX, version; version NN, GUI screen data n". When the medical device 302 is turned on, it transmits the "model name: XXX, version NN" as identification information D to the controller 301 (S21). Upon receipt of the identification information D (YES in S22), the controller 301 searches the GUI screen data identification table 500 in the storage unit 203, and determines whether or not it includes the GUI screen data corresponding to the model name and version name of the identification information D (S23). When it stores the GUI screen data corresponding to the model name and the version name of the identification information D (YES in S23), the controller 301 structures the GUI using the GUI screen data, and displays it on the display unit 303 (S29).

If the table does not store the GUI screen data corresponding to the model name and the version name of the identification information D (NO in S23), then the controller 301 requests the medical device 302 to transmit the GUI screen data corresponding to the identification information D (S24).

When the medical device 302 receives the transmission request (YES in S25), it transmits the GUI screen data corresponding to the identification information D (S26).

The controller 301 receives the GUI screen data (YES in S27), it associates the received GUI screen data 6 with the identification information D and stores the data in the GUI screen data identification table 500 (S28). Furthermore, the controller 301 structures a GUI using the GUI screen data, and displays it on the display unit 303 (S29).

Thus, the medical device 302 has the function of transmitting identification information (model name, version, etc.) to the controller 301. When the controller 301 receives identification information from the medical device 302, it confirms whether or not the GUI screen data identification table 500 includes the GUI screen data corresponding to the identification information. When the table includes the GUI screen data corresponding to the identification information, the controller 301 structures a GUI screen using the GUI screen data. If the table does not include the GUI screen data corresponding to the identification information, then the controller 301 requests the medical device 302 to transmit GUI screen data. The controller associates the GUI screen data received from the medical device with identification information, and stores the data in the GUI screen data identification table 500.

Thus, the medical control system according to the present embodiment includes the medical device 302, a medical control apparatus (controller 301) for controlling the medical device, and a display operation device (display unit 303) for controlling the medical device.

The medical device has a GUI image data storage unit and transmission unit. The GUI image data storage unit (storage unit 312) stores a graphical user interface (GUI) image data to be displayed on the display operation device, and identification information for identification of the GUI screen data. The transmission unit (communication I/F 313) transmits the identification information. The identification information includes the model name of the medical device and version information about the GUI image data.

The medical control apparatus includes a GUI image data identification storage unit, a determination unit, a GUI generation unit, and an output unit. The GUI image data identification storage unit (storage unit 203) stores the identification information, and the GUI image data corresponding to the identification information. The determination unit (control unit 201) determines whether or not identification information matching the identification information transmitted from the medical device is stored in the GUI image data identification storage unit. If it is determined that the identification information matching the received identification information is stored in the GUI image data identification storage unit, then the GUI generation unit (GUI generation unit 202) generates a GUI image based on the GUI image data corresponding to the identification information. The output unit (display I/F 206) outputs the generated GUI image to the display operation device.

With the above-mentioned configuration, since data transmission is not performed for the GUI image data already stored in the controller 301, the communication load and the processing time required to display data can be reduced.

Furthermore, if the identification information matching the received identification information is not stored in the storage unit, then the determination unit requests the medical device to transmit the GUI image data corresponding to the identification information. The GUI image data storage unit associates the GUI data transmitted from the medical device at the request with the identification information and stores the data. The GUI generation unit generates GUI image based on the GUI image data transmitted from the medical device at the request.

With the above-mentioned configuration, only the GUI image data not held by the controller 301 is transmitted, an average communication load and the processing time required for display can be reduced.

According to the present embodiment, even when a plurality of medical devices 302 are simultaneously turned on, GUI screen data is not transmitted to any medical devices 302 except the first connected medical device 302. Therefore, the amount of data received and processed by the controller 301 can be reduced, thereby avoiding a heavy load on the CPU (central processing unit). Since the communication time and the processing time can be shortened, an operation can be smoothly performed. Furthermore, the controller 301 requires no high-performance communication module or CPU, thereby suppressing the cost of the controller 301.

In the present embodiment, image data is used as GUI screen data. However, the present invention is not limited to this application. That is, for example, the GUI screen parameter information according to the first embodiment can be used.

Third Embodiment

Described below according to the present embodiment is the medical control apparatus for first displaying the GUI data having a small amount of data and relating to a more frequently used function on the GUI screen, and displaying after a lapse of a predetermined time the GUI data having a large amount of data and relating to a less frequently used function on the GUI screen. Since the system environment of the present embodiment is similar to those shown in FIGS. 2 and 3, the detailed explanation is omitted here.

Conventionally, a medical device has collectively transmitted image data of all screens of the GUI for all functions. Therefore, the controller cannot display the operation screen of the medical device or perform any operation before receiving all data.

Figure 10:
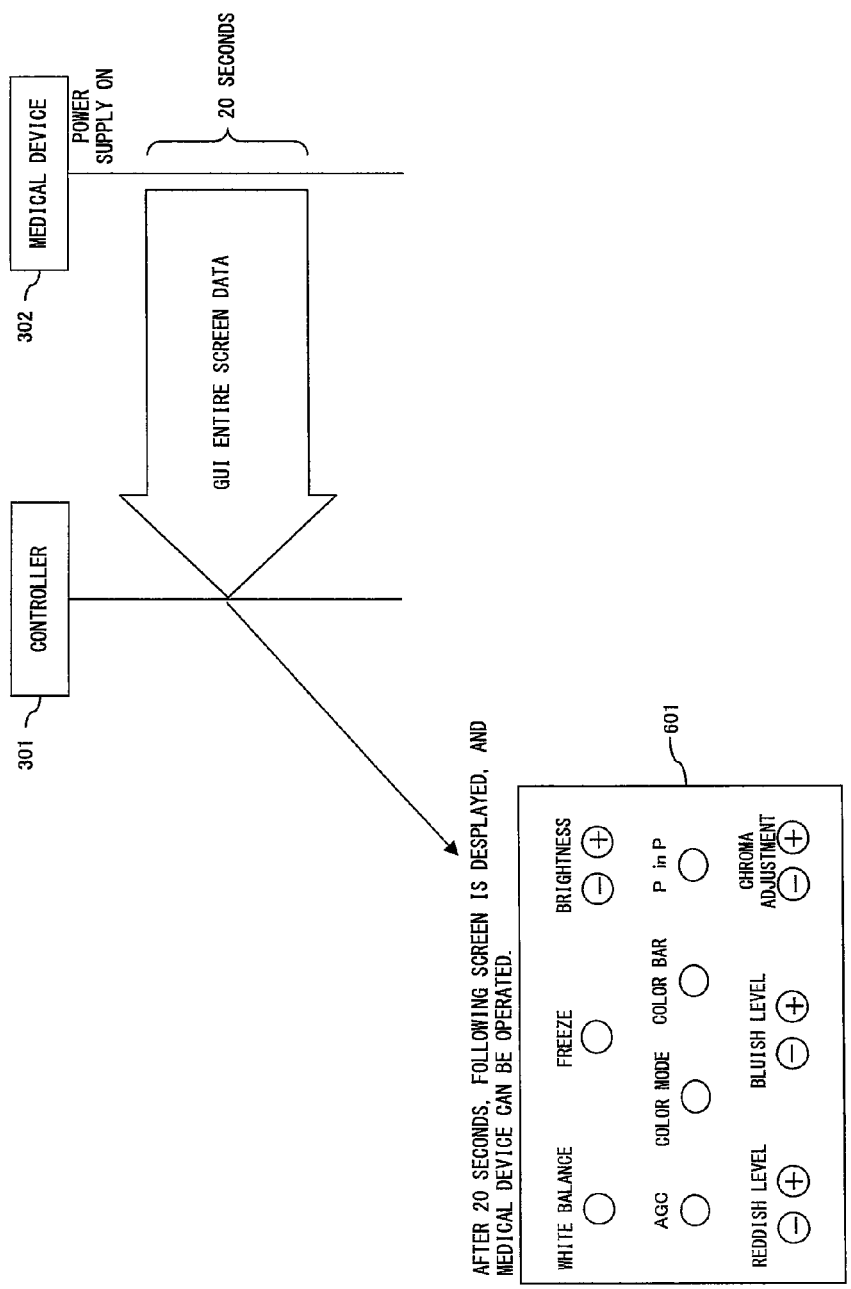
FIG. 10 is an explanatory view showing the flowchart of displaying GUI screen data transmitted from the conventional medical device to the controller on the display unit.

FIG. 10 is an explanatory view of the flow until the GUI screen data transmitted from a conventional medical device to a controller is displayed on the display unit. In FIG. 10, it takes 20 seconds for the medical device 302 to completely transmit the GUI screen data. After completely receiving the GUI image data after the lapse of the 20 seconds, the controller generates GUI image based on the GUI image data. The generated GUI screen image 601 is output to the display unit 303, and displayed on the display unit 303. Thus, the operation of the display unit 303 can be performed.

Figure 11:
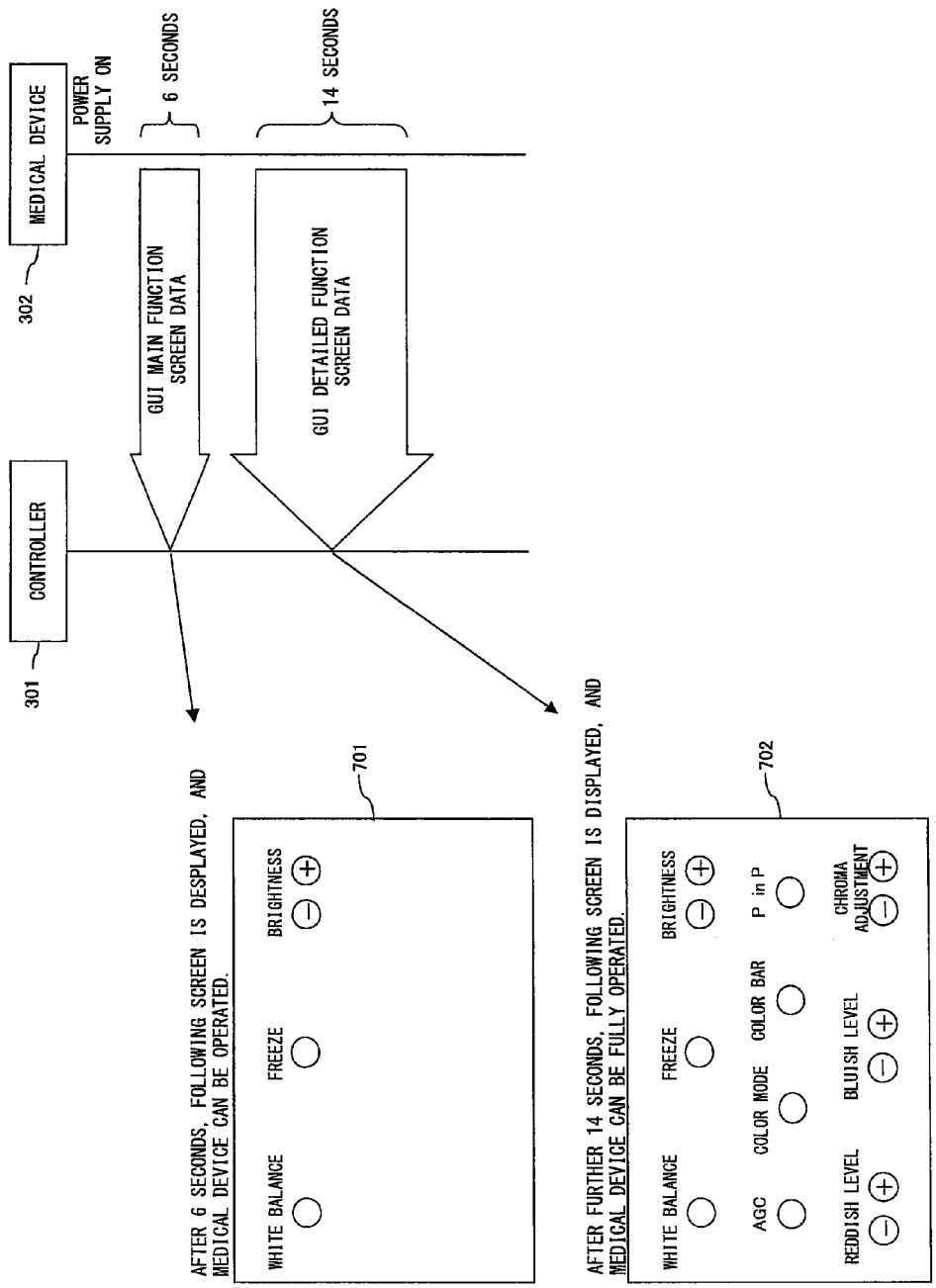
FIG. 11 is an explanatory view showing a flowchart of displaying GUI screen data transmitted from the medical device according to the third embodiment to the controller on the display unit.

FIG. 11 is an explanatory view of the flow until the GUI screen data transmitted from the medical device to the controller according to the present embodiment is displayed on the display unit. The medical device 302 separately stores in advance in the storage unit 312 the GUI main function screen data (in small data quantity) with which only more frequently used functions can be operated, and the GUI detailed function screen data (in large data quantity) with which less frequently used functions can be operated.

When the medical device 302 is turned on, the control unit 311 of the medical device 302 sequentially transmits the GUI main function screen data and the GUI detailed function screen data to the controller 301. Assume that it respectively takes, for example, 6 seconds and 14 seconds to transmit the GUI main function screen data and the GUI detailed function screen data.

The controller 301 receives the GUI main function screen data and the GUI detailed function screen data through the communication I/F 205. When the control unit 201 completes receiving the GUI main function screen data, it transmits the GUI main function screen data to the GUI generation unit 202. The GUI generation unit 202 generates a main function operation screen image 701 based on the GUI screen data 1 without waiting for the completion of the reception of the GUI detailed function screen data. The generated main function operation screen image 701 is output through the display I/F 206, and displayed on the display unit 303. Thus, only the main function of the medical device can be controlled using the display unit 303.

Then, after the control unit 201 completes the reception of the GUI detailed function screen data, it transmits the GUI main function screen data to the GUI generation unit 202. The GUT generation unit 202 generates a detailed function operation screen image based on the GUI screen data 1, and adds the image to the main function operation screen image 701, thereby structuring a detailed function operation screen image 702. The detailed function operation screen image 702 is output to the display unit 303 through the display I/F 206, and displayed on the display unit 303. Thus, all functions of the medical device can be used through the display unit 303.

Then, the functions more frequently used in an operation (white balance, freeze, brightness, etc.) can be operated in a short period after the medical device 302 is turned on, thereby proceeding with a smooth operation.

Figure 12:
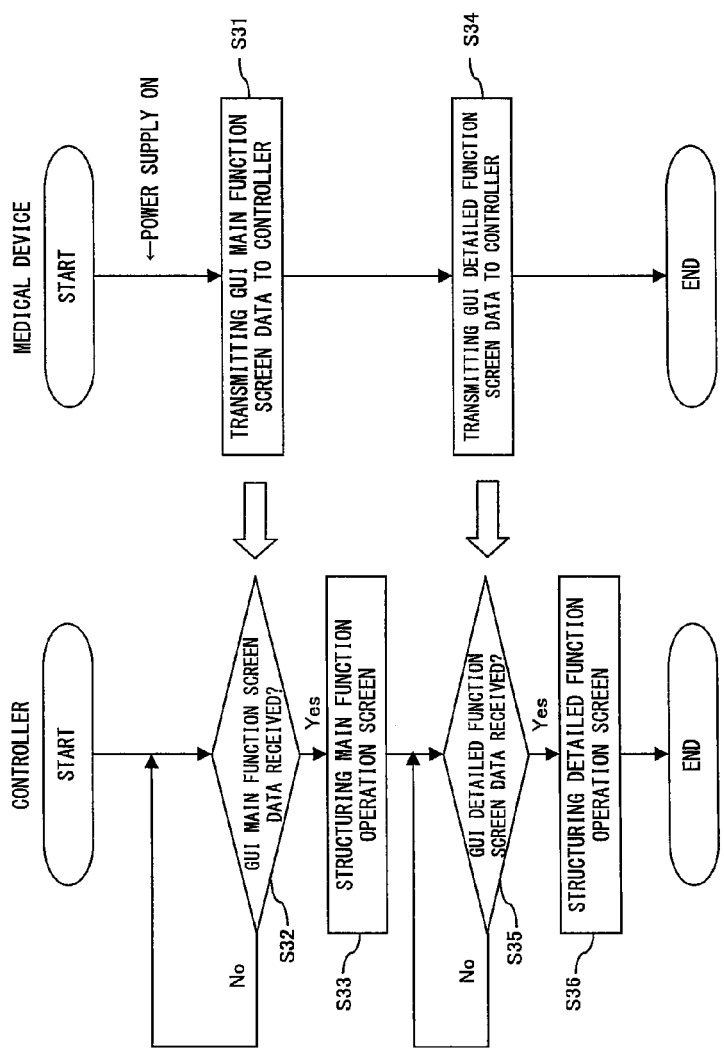
FIG. 12 is an operation flowchart of the controller and the medical device according to the third embodiment.

FIG. 12 shows an operation flowchart of the controller 301 and the medical device 302 according to the present embodiment. The medical device 302 transmits the GUI main function screen data to the controller 301 when it is turned on (S31).

When the controller 301 receives the GUI main function screen data (YES in S32), it structures an operation screen on which main functions can be operated using the GUI main function screen data, and displays it on the display unit 303 (S33).

Furthermore, the medical device 302 transmits the GUI detailed function screen data to the controller 301 (S34). When the controller 301 receives the GUI detailed function screen data (YES in S35), it structures an operation screen on which a detailed function can be operated using the GUI detailed function screen data, and displays the screen on the display unit 303 (S36).

Thus, the medical device 302 has GUI main function screen data (in small data quantity) and GUI detailed function screen data (in large data quantity), and sequentially transmits them to the controller 301. When the controller 301 receives the GUI main function screen data, it structures a main function operation screen. When the controller 301 receives the GUI detailed function screen data, it structures a detailed function operation screen. When the main function operation screen is displayed, the main function operation screen can be operated even while the controller 301 is receiving the GUI detailed function screen data.

As described above, the medical control system includes the medical device 302, a medical control apparatus (controller 301) for controlling the medical device, and a display operation device (display unit 303).

The medical device includes a storage unit and a transmission unit. The storage unit stores first GUI screen data relating to a predetermined function in the GUI screen data configuring the graphical user interface (GUI) for controlling the medical device, and second GUI screen data (GUI detailed function screen data) as GUI screen data other than the first GUI screen data. The transmission unit sequentially transmits the first GUI screen data and the second GUI screen data. The first GUI screen data is the GUI screen data (GUI main function screen data) relating to the main function of the medical device. The second GUI screen data is GUI screen data (GUI detailed function screen data) relating to the detailed function of the medical device.

The medical control apparatus includes a reception unit (communication I/F 205), a GUI generation unit (GUI generation unit 202), and an output unit (display I/F 206). The reception unit sequentially receives the first GUI screen data and the second GUI screen data. The GUI generation unit generates a GUI screen image based on the received GUI screen data. The output unit outputs the GUI screen image to the display operation unit.

The GUI generation unit generates a first GUI screen image based on the first GUI screen data after the completion of the reception of the first GUI screen data, displays the image on the display operation unit, and generates a second GUI screen image based on the first GUI screen data and the second GUI screen data after the completion of the reception of the second GUI screen data, thereby displaying the image on the display operation unit.

With the above-mentioned configuration, the medical device can be operated from the time when the main function screen is displayed after the GUI main function screen data in a small data quantity is completely received.

According to the present embodiment, although a plurality of medical devices are simultaneously turned on, a medical device can be operated when the main function screen is displayed after the GUI main function screen data in a small data quantity is completely received. Therefore, the time taken to become possible to control the main function of a medical device is short, and a smooth operation can be continued.

The present embodiment can be applied to the first embodiment. That is, the GUI screen parameter information about the screen component of a main function can be used as GUI main function screen data, and the GUI screen parameter information about the screen component of a detailed function can be used as GUI detailed function screen data.

The present invention is not limited to the above-mentioned embodiments, but various configurations and embodiments can be applied within the gist of the present invention.

What is claimed is:

1. A medical control system having a medical device, a medical control apparatus for controlling the medical device, and a display operation device for controlling the medical device, wherein:
the medical device comprises:
a GUI setting information storage unit storing GUI setting information as setting information relating to design of a GUI screen configuring a graphical user interface (GUI) for controlling the medical device;
a GUI setting information transmission unit transmitting the GUI setting information to the medical control apparatus, and the medical control apparatus comprises:
a GUI generation unit generating a GUI screen image according to the transmitted GUI setting information; and
an output unit outputting the generated GUI screen image to the display operation device,
wherein
the GUI setting information includes a plurality of pieces of GUI screen parameter information, and each of the plurality of pieces of GUI screen parameter information is a text parameter for drawing each of piece of image data of a plurality of parts configuring the GUI screen image, and
the GUI generation unit
generates image data of each part from each of the plurality of pieces of GUI screen parameter information, and
generates the GUI screen image by combining the generated image data of the parts.

2. The system according to claim 1, wherein
the GUI setting information comprises at least:
first GUI screen parameter information including a text parameter for drawing background image data of the GUI screen image,
second GUI screen parameter information including a text parameter for drawing set value display area image data of the GUI screen image, and
third GUI screen parameter information including a text parameter for drawing operation button image data of the GUI screen image, and
the GUI generation unit
generates at least the background image data, the set value display area image data, and the operation button image data from the first GUI screen parameter information, the second GUI screen parameter information, and the third GUI screen parameter information, respectively, and
generates the GUI screen image by combining the generated image data.

3. The system according to claim 1 wherein
the plurality of pieces of GUI screen parameter information includes a plurality pieces of the GUI screen parameter information of a main function of the medical device and a plurality pieces of GUI screen parameter information of a detailed function of the medical device,
the GUI setting information transmission unit
firstly transmits the plurality pieces of GUI screen parameter information of the main function of the medical device, and
secondly transmits the plurality of pieces of GUI screen parameter information of the detailed function of the medical device, and
the GUI generation unit
generates image data of each part from each of the plurality pieces of GUI screen parameter information of the main function of the medical device after completely receiving the plurality pieces of the GUI screen parameter information of the main function of the medical device, and generates first GUI screen image which is a screen image relating to the main function of the medical device by combining the generated image data of the parts to display the generated first GUI screen image on the display operation device, and
generates image data of each part from each of the plurality pieces of GUI screen parameter information of the main function of the medical device and the plurality pieces of GUI screen parameter information of the detailed function of the medical device after completely receiving the plurality pieces of GUI screen parameter information of the detailed function of the medical device, and generates a second GUI screen image which is a screen image relating to all functions of the medical device by combining the generated image data of the parts to display the generated second GUI screen image on the display operation device.

4. A medical control apparatus, comprising:
a reception unit receiving GUI setting information transmitted from a medical device as setting information relating to a design of a GUI screen configuring a graphical user interface (GUI) for controlling the medical device;
a GUI generation unit generating a GUI screen image according to the GUI setting information;
an output unit outputting the generated GUI screen image to the display operation device,
wherein
the GUI setting information includes a plurality of pieces of GUI screen parameter information, and each of the plurality of pieces of GUI screen parameter information is a text parameter for drawing each piece of image data of a plurality of parts configuring of the GUI screen image, and
the GUI generation unit
generates image data of each part from each of the plurality of pieces of GUI screen parameter information, and
generates the GUI screen image by combining the generated image data of the parts.

5. The apparatus according to claim 4, wherein
the GUI setting information includes at least:
first GUI screen parameter information having a text parameter for drawing background image data of the GUI screen image;
second GUI screen parameter information having a text parameter for drawing set value display area image data of the GUI screen image; and
third GUI screen parameter information having a text parameter for drawing operation button image data of the GUI screen image, and
the GUI generation unit
generates at lest the background image data, the set value display area image data, and the operation button image data from the first GUI screen parameter information, the second GUI screen parameter information, and the third GUI screen parameter information, respectively, and generates the GUI screen image by combining the generated image data.

6. The apparatus according to claim 4, wherein
the plurality of pieces of GUI screen parameter information includes a plurality pieces of GUI screen parameter information of a main function of the medical device and a plurality pieces of GUI screen parameter information of a detailed function of the medical device,
the GUI generation unit
generates image data of each part from each of the plurality pieces of GUI screen parameter information of the main function of the medical device after completely receiving the plurality pieces of GUI screen parameter information of the main function of the medical device, and generates first GUI screen image which is a screen image relating to the main function of the medical device by combining the generated image data of the parts to display the generated first GUI screen image on the display operation device, and
generates image data of each part from each of the plurality pieces of GUI screen parameter information of the main function of the medical device and the plurality pieces of GUI screen parameter information of the detailed function of the medical device after completely receiving the plurality pieces of GUI screen parameter information of the detailed function of the medical device, and generates a second GUI screen image which is a screen image relating to all functions of the medical device by combining the generated image data of the parts to display the generated second GUI screen image on the display operation device.

7. A medical control system having: a medical device; a medical control apparatus for controlling the medical device; and a display operation device for controlling the medical device, wherein:
the medical device comprises:
a GUI image data storage unit storing graphical user interface (GUI) image data to be displayed on the display operation device, and identification information for identification of the GUI image data; and
a transmission unit transmitting the identification information, and the medical control apparatus comprises:
a GUI image data identification storage unit storing the identification information and GUI image data corresponding to the identification information;
a determination unit determining whether or not identification information matching the identification information transmitted from the medical device is stored in the GUI image data identification storage unit;
a GUI generation unit generating a GUI image based on a determination result by the determination unit; and
an output unit outputting the generated GUI image to the display operation device,
wherein
when it is determined by the determination unit that identification information matching the identification information transmitted from the medical device is stored in the GUI image data identification storage unit,
the GUI generation unit generates the GUI image based on the GUI image data corresponding to the identification information stored in the GUI image data identification storage unit, and
when it is determined by the determination unit that identification information matching the identification information transmitted from the medical device is not stored in the GUI image data identification storage unit,
the determination unit requests the medical device to transmit GUI image data corresponding to the identification information,
the GUI image data identification storage unit associates the GUI image data transmitted from the medical device at the request with the identification information and stores the data, and
the GUI generation unit generates the GUI image based on the GUI image data transmitted from the medical device at the request.

8. The system according to claim 7, wherein
the identification information comprises a model name of the medical device and version information about the GUI image data.

9. A medical control apparatus, comprising:
a GUI image data identification storage unit storing graphical user interface (GUI) image data and identification information for identification of the GUI image data;
a determination unit receiving identification information transmitted from a medical device, and determining whether or not identification information matching the identification information is stored in the GUI image data identification storage unit;

a GUI generation unit generating a GUI image based on a determination result by the determination unit; and an output unit outputting the generated GUI image to the display operation device, wherein when it is determined by the determination unit that identification information matching the identification information transmitted from the medical device is stored in the GUI image data identification storage unit, the GUI generation unit generates the GUI image based on the GUI image data corresponding to the identification information stored in the GUI image data identification storage unit, and when it is determined by the determination unit that identification information matching the identification information transmitted from the medical device is note stored in the GUI image data identification storage unit, the determination unit requests the medical device to transmit GUI image data corresponding to the identification information, the GUI image data identification storage unit associates the GUI image data transmitted from the medical device at the request with the identification information and stores the data, and the GUI generation unit generates the GUI image based on the GUI image data transmitted from the medical device at the request.

10. The apparatus according to claim 9, wherein identification information comprises a model name of the medical device and version information about the GUI image data.

11. A medical control system having a medical device, a medical control apparatus for controlling the medical device, and a display operation device for controlling the medical device, wherein:

the medical device comprises:

a storage unit storing first GUI screen data relating to a main function of the medical device in GUI image data configuring a graphical user interface (GUI) for controlling the medical device, and second GUI screen data relating to a detailed function of the medical device other than the first GUI screen data;

a transmission unit sequentially transmitting the first GUI screen data and the second GUI screen data in this order; and the medical control apparatus includes:

a reception unit for sequentially receiving the first GUI screen data and the second GUI screen data;

a GUI generation unit generating GUI screen image based on the received GUI screen data; and an output unit outputting the GUI screen image to the display operation unit, and after completely receiving the first GUI screen data, the GUI generation unit generates the first GUI screen image relating to the main function of the display device based on the first GUI screen data, and displays the image on the display operation unit, and after completely receiving the second GUI screen data, the second GUI screen image relating to all functions of the medical device is generated based on the first GUI screen data and the second GUI screen data, and displayed on the display operation unit.

12. The system according to claim 11, wherein the main function has a higher usage frequency than the detailed function.

13. A medical control apparatus, comprising:

a reception unit sequentially receiving first GUI screen data relating to a main function of a medical device in GUI image data configuring a graphical user interface (GUI) for controlling the medical device, and second GUI screen data relating to a detailed function of the medical device other than the first GUI screen data;

a GUI generation unit generating a GUI screen image based on the received GUI screen data; and an output unit outputting the GUI screen image to the display operation unit, wherein the GUI generation unit generates a first GUI screen image relating to a main function of the medical device based on the first GUI screen data after completion of reception of the first GUI screen data, and displays the image on the display operation unit, and generates a second GUI screen image relating to all functions of the medical device based on the first GUI screen data and the second GUI screen data after completion of reception of the second GUI screen data, and displays the image on the display operation unit.

14. The apparatus according to claim 13, wherein the main function has a higher usage frequency than the detailed function.

* * * * *